US00PP14936P2

(12) United States Plant Patent
Christensen

(10) Patent No.: US PP14,936 P2
(45) Date of Patent: Jun. 22, 2004

(54) FLORIBUNDA ROSE PLANT NAMED 'CHRISGOOD'

(50) Latin Name: *Rosa hybrida*
Varietal Denomination: Chrisgood

(75) Inventor: Jack E. Christensen, Ontario, CA (US)

(73) Assignee: CP (Delaware), Inc., Wilmington, DE (US)

( * ) Notice: Subject to any disclaimer, the term of this patent is extended or adjusted under 35 U.S.C. 154(b) by 0 days.

(21) Appl. No.: 10/183,517

(22) Filed: Jun. 28, 2002

(51) Int. Cl.[7] ..... A01H 5/00
(52) U.S. Cl. ..... Plt./143
(58) Field of Search ..... Plt./143, 142

(56) References Cited

U.S. PATENT DOCUMENTS

PP13,757 P2 * 4/2003 Meilland ..... Plt./142

OTHER PUBLICATIONS

Anonymous. "Modern Magic 'Chirsgood'" http://www.star-roses.com/viewrose.cfm?RoseID=169 1999.*
Anonymous. HelpMeFind Rose: CHRisgood http://www.helpmefind.com/rose/pl.php?n=20917.*
UPOV ROM GTITM Computer Database, GTI JOUVE Retrieval Software 2003/01 citation for 'Chrisgood'.*
Morrison Gardens Class: Floribunda http://www.rkdn.org/roses/classes.asp?ID=(5).*
Protection Des Obtentions Vegetables, Bulletin Officiel du Comité de la Protection des Obtentions Végétales, No. 8 and 9, Cover Page and p. 334 (1999).

* cited by examiner

*Primary Examiner*—Bruce R. Campell
*Assistant Examiner*—W C Haas
(74) *Attorney, Agent, or Firm*—Burns, Doane, Swecker & Mathis, L.L.P.

(57) ABSTRACT

A new and distinct variety of Floribunda rose plant is provided which abundantly forms double flat cup-shaped bright multi-colored blossoms. The blossoms display a distinctive random mixture of streaks and spots of red, orange, and yellow on the upper petal surfaces. The plant exhibits an upright bushy growth habit. The foliage is medium to dark green and semi-glossy and contrasts nicely with the multi-colored blossoms. The new variety is particularly well suited for growing as attractive ornamentation in an informal garden setting.

1 Drawing Sheet

Figures 1, 2, 3, 4, 5, 6, 7, 8, 9, 10, 11, 12, 13, 14, 15, 16, 17:
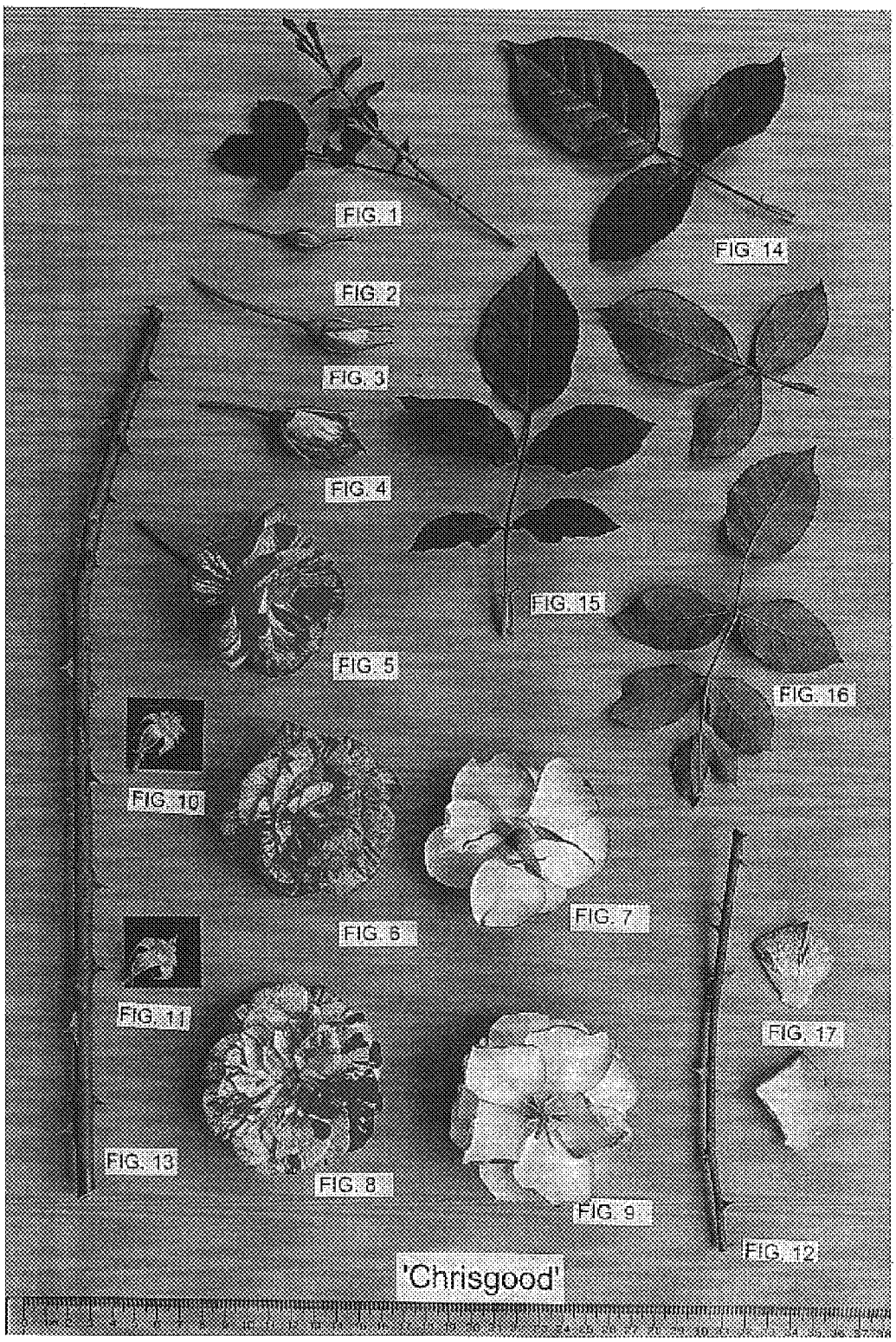

Botanical/commercial classification: Rosa hybrida/Floribunda Rose Plant.
Varietal denomination: 'Chrisgood'.

SUMMARY OF THE INVENTION

The new variety of Rosa hybrida Floribunda rose plant was created by artificial pollination wherein two parents were crossed which previously had been studied in the hope that they would contribute the desired characteristics. The female parent (i.e., the seed parent) was the 'Aromiclea' variety (U.S. Plant Pat. No. 6,121). The 'Aromiclea' variety is marketed under the VODOO trademark. The male parent (i.e., the pollen parent) was the 'JACtiger' variety (non-patented in the United States). The 'JACtiger' variety sometimes is known as 'JACtang' and as 'Tiger Tail'. The parentage of the new variety can be summarized as follows:

'Aromiclea'×'JACtiger'

The seeds resulting from the above pollination were sown and small plants were obtained which were physically and biologically different from each other. Selective study resulted in the identification of a single plant of the new variety.

It was found that the new Floribunda rose variety of the present invention exhibits the following combination of characteristics:

(a) an upright bushy growth habit,
(b) abundantly forms attractive double flat cup-shaped bright multiple-colored blossoms that are a distinctive random mixture in streaks and spots of red, orange, and yellow on the upper petal surfaces,
(c) forms medium to dark green semi-glossy foliage, and
(d) is particularly well suited for growing as ornamentation in an informal garden setting.

The disease resistance is good with respect to common rose diseases. The foliage coloration contrasts nicely that of the multi-colored blossoms.

The new variety well meets the needs of the horticultural industry and can be used to advantage for growing in the landscape where distinctive coloration is sought in a perennial or informal garden design.

The new variety of the present invention can be readily distinguished from its ancestors. For instance, both of its parents are dissimilar Hybrid Tea rose varieties. The 'Aromiclea' variety forms large flowers that display a blend of salmon, yellow, orange and pink. The 'JACtiger' variety forms flowers with deep orange, white or cream-colored stripes.

The new variety has been found to undergo asexual propagation by budding and grafting at Ontario, Calif. and West Grove, Pa. Such asexual propagation by the above-mentioned techniques has shown that the characteristics of the new variety are stable and are strictly transmissible by such asexual propagation from one generation to another.

The new variety has been named the 'Chrisgood' variety.

BRIEF DESCRIPTION OF THE PHOTOGRAPH

The accompanying photograph shows as nearly true as it is reasonably possible to make the same, in a color illustration of this character, typical specimens of the new variety. The rose plants of the new variety were approximately two years of age and were observed during July 2003 while growing on Rosa 'Dr. Huey' understock in containers in an unheated greenhouse at West Grove, Pa.

FIG. 1—illustrates a specimen of a young shoot;

FIG. 2—illustrates a specimen of a floral bud before the opening of the sepals;

FIG. 3—illustrates a specimen of a floral bud at the opening of the sepals;

FIG. 4—illustrates a specimen of a floral bud at the opening of the petals;

FIG. 5—illustrates a specimen of a flower in the course of opening;

FIG. 6—illustrates a specimen of an open flower—plan view—obserse;

FIG. 7—illustrates a specimen of an open flower—plan view—reverse;

FIG. 8—illustrates a specimen of a fully open flower—plan view—obverse;

FIG. 9—illustrates a specimen of a fully open flower—plan view—reverse;

FIG. 10—illustrates a specimen of a floral receptacle showing the arrangement of the stamens and pistils;

FIG. 11—illustrates a specimen of a floral receptacle showing the arrangement of the pistils (stamens removed);

FIG. 12—illustrates a specimen of the upper section of a young flowering stem displaying prickles and without foliage;

FIG. 13—illustrates a specimen of the middle lower section of a flowering stem displaying prickles and without foliage;

FIG. 14—illustrates a specimen of leaves with three leaflets—plan view—upper surface (upper specimen) and under surface (lower specimen);

FIG. 15—illustrates a specimen of a leaf with five leaflets—plan view—upper surface;

FIG. 16—illustrates a specimen of a leaf with seven leaflets—plan view—lower surface; and FIG. 17—illustrates specimens of maturing plants—plan view—upper surface (upper specimen) and under surface (lower specimen).

DETAILED DESCRIPTION

The chart used in the identification of the colors is that of The Royal Horticultural Society (R.H.S. Colour Chart). The description is based on the observation of two year-old plants during June 2002 and subsequently during July 2003, and September 2003 while budded on Rosa 'Dr. Huey' understock and growing in containers outdoors at West Grove, Pa.

Class: Floribunda.

Plant:

*Height.*—Approximately 65 to 75 cm on average at the end of the growing season.

*Width.*—Approximately 50 to 65 cm on average at the end of the growing season.

*Habit.*—Upright and bushy.

Branches:

*Color.*—Young stems: near Green Group 138A. adult wood: near Green Group 138B.

*Thorns.*—The thorns are variable and generally can be classified in the indicated categories with the following commonly being observed on a typical vigorous flowering stem of 15 cm length and 10 to 12 mm in diameter. Major thorns: approximately 10 to 13 (average approximately 12) in number, approximately 9.5 to 14 mm (average approximately 12 mm) in length at the base parallel to the stem axis, approximately 2.8 to 3.8 mm (approximately 3.4 mm) in width perpendicular to the stem axis, and approximately 8.5 to 10 mm (average 9 mm) in vertical height. Minor thorns: approximately 19 to 23 (average approximately 21) in number, approximately 3.8 to 7 mm (average approximately 5 mm) in length at the base parallel to the stem axis, approximately 1.15 to 2 mm (average approximately 1.4 mm) in width perpendicular to the stem axis, and approximately 3 to 6.6 mm (average approximately 5 mm) in vertical height. Minute thorns: approximately 60 to 100+ (approximately 85 on average in number, approximately 1.5 to 2.3 mm (average approximately 2 mm) in length at the base parallel to the stem axis, approximately 0.5 to 0.95 mm (approximately 0.8 mm on average) perpendicular to the stem axis, and approximately 1.5 to 2.8 mm (approximately 2.5 mm) in vertical height. Glandular hairs: relatively stiff, commonly are present on stems, petioles, rachis, petiolules, stipules, peduncles, receptacles and sepals in a highly variable quantity, the size commonly ranges from less than 0.2 mm to approximately 8 mm in height, and the gland appears to secrete when very young and to become non-functioning with maturity. Attachment: the thorns commonly are firmly attached. Orientation: major thorns tend to curve and to point to the base of the stem with the upper and lower edges being somewhat concave, the minor and minute thorns tend to be more upright and more perpendicular to the stems, and the stiff glandular hairs are disposed substantially perpendicular to the stems. Color: on upper areas of flowering shoots immature thorns commonly are Yellow-Green Group 144B to 144C and exhibit some red coloration of near Greyed-Purple Group 187B and 187C with small amounts of Greyed-Purple Group 185A, 186A through 187A with the red coloration being somewhat transparent and to appear to overlay the yellow-green base coloration, and more mature thorns commonly are near Brown Group 200C at the base, lightening to Brown Group 200D upwards, and commonly darkening through Brown Group 200B and 200A at the tip. More mature thorns commonly also include some coloration near Greyed-Orange Group 165A at the base shading continuously from Greyed-Orange Group 165B through and near Greyed-Orange Group 164A and Greyed-Orange Group 166C at the tip. The stiff glandular hairs are tipped with a reddish gland of near Greyed-Purple Group 185A to 187C.

Leaves:

*Petioles.*—Length: for a three-leaflet leaf commonly approximately 20 to 50 mm (approximately 35 mm on average), for a five-leaflet leaf commonly approximately 34 to 56 mm (approximately 40 mm on average), and for a seven-leaflet leaf approximately 20 to 36 mm (approximately 29 mm on average). Diameter: for a three-leaflet leaf 1 to 1.9 mm (approximately 1.3 mm on average), for a five-leaflet leaf approximately 1.7 mm, and for a seven-leaflet leaf approximately 1.8 mm. Texture: some minute prickles that are hooked towards the base commonly are present on the lower surface and along the midrib including the portion of the petiole that supports the stipule. These appear to be more common on five- and seven-leaflet leaves and rarely are found scattered on the upper surface. Color: the upper surface is primarily Yellow-Green Group 144A with some lightening to near Yellow-Green Group 144B, and the lower surface is primarily Yellow-Green Group 144B with some darkening to near Yellow-Green Group 144A. Some red pigmentation near and through Greyed-Purple Group 185A, 187A, 187B, and 187C may be present on mature leaf petioles.

*Rachis.*—Length: for a five-leaflet leaf commonly approximately 17 to 30 mm (approximately 23 mm on average), and for a seven-leaflet leaf commonly approximately 38 to 51 mm (approximately 47 mm on average). Diameter: for a five-leaflet leaf approximately 1.01 to 1.65 mm (approximately 1.5 mm on average) and for a seven-leaflet leaf approximately 1.3 to 1.52 mm (approximately 1.45 mm on average). Texture: commonly bears approximately 2 to 4 (3 on average) minute hooked prickles having heights of approximately 1.5 to 2 mm on the lower surface, and some sparsely scattered red-tipped stiff glandular hairs on both surfaces. Color: substantially the same as that of the petiole.

*Petiolule.*—Length: approximately 9 to 22 mm for all leaf types with an average of approximately 14 mm for a three-leaflet leaf, approximately 15.5 mm for a five-leaflet leaf, and approximately 17 mm for a seven-leaflet leaf. Diameter: approximately 0.9 to 1.44 (approximately 1.1 mm on average) for all leaf types. Texture: commonly bears approximately 1 or 2 minute prickles on the lower surface similar to those found on the rachis as well as some similar sparsely scattered red-tipped glandular hairs on both surfaces. Color: substantially the same as that of the petiole and rachis.

*Leaflets.*—Number: 3, 5, and 7. Shape: elliptic to broadly elliptical, occasionally somewhat obovate to narrowly elliptical to rarely oblong. Size: terminal leaflets commonly measure approximately 3.5 to 8.5 cm in length and approximately 2 to 5 cm in width on average with greatest dimensions commonly being exhibited by three-leaflet leaves. Serration: serrate to serulate. Apex: abruptly acuminate to occasionally broadly acute. Base: cuneate to broadly cuneate to almost rounded or slightly oblique. Texture: upper and lower surfaces are near glabrous, and occasionally bear widely scattered pilose hairs on or near the larger venation. Venation: pinnate and reticulate, and near Yellow-Green Group 146B on the upper surface, and on the lower surface substantially the same as the leaf color with some darkening at the midrib and lightening as the vein becomes larger. The darker areas commonly are near Yellow-Green Group 146B shading from near and through Yellow-Green Group 144A, 144B, and 144C. Color (adult foliage): upper surface: near Green Group 139A. under surface: near Green Group 138A shading to near and through Green Group 137C and 138B.

*Leaves.*—Size: varies greatly and is influenced by the vigor of the developing shoot, the time of the year and other cultural and environmental factors. Dimensions for typical leaves are presented hereafter and leaves having dimensions well outside the ranges presented can be observed and are considered to be non-typical. The length of the pinnately compound leaves is measured from the tip of the terminal leaflet to the furthest point of the petiole base. The width is measured across the largest leaflet pair from tip to tip (typically the leaflet set immediately below the terminal leaflet). Three-leaflet leaves: commonly approximately 7 to 15.5 cm (approximately 10.5 cm on average) in length and approximately 6 to 13 cm (approximately 9.2 cm on average) in width. Five-leaflet leaves: commonly approximately 11 to 17.5 cm (approximately 14.2 cm) in length and approximately 7 to 12.5 cm (approximately 10.2 cm on average) in width. Seven-leaflet leaves: commonly approximately 14.5 to 17 cm (approximately 15 cm on average) in length and approximately 8.7 to 11 cm (approximately 9.6 cm on average) in width.

*Stipules.*—Shape: relatively straight sided with the projecting wing tip typically being substantially perpendicular to the petiole axis. Length: commonly approximately 1.5 to 2.7 cm to the furthest wing tip with the greatest length commonly being observed on five-leaflet leaves. Width: commonly approximately 3 to 6.5 mm with the greatest width commonly being observed on five-leaflet leaves. Spread: the spread of the wing tips commonly ranges from approximately 6 to 13 mm with the greatest spread commonly being observed on five-leaflet leaves. Texture: glandular hairs commonly are scattered on the lower surface and rarely are found on the upper surface. Margins: lined with glandular hairs commonly ranging in height from 0.15 to 0.4 mm. The tips of such hairs are reddish and are near Greyed-Purple Group 185A and 187C in coloration. Color: the stipule body commonly is near Green Group 141C to Yellow-Green Group 144A and 144B.

Inflorescence:

*Number of flowers.*—1 to 3 blooms per stem are common, commonly borne in clusters, and up to approximately 5 blooms in a cluster sometimes are formed.

*Sepals.*—five per flower, long and tapering, commonly range from approximately 1.9 to 3.3 cm (approximately 2.6 cm on average) in length with some sepals having 2 or 3 thin elongated extensions projecting from the edges. The sepals commonly extend well beyond the main body of the bud. The width commonly is approximately 5.5 to 10 mm (approximately 8 mm on average) at the widest point. The outer surface commonly bears a few scattered glandular hairs. The color of the outer surface is primarily near Green Group 143A shading near and through Green Group 143B and 143C and Yellow-Green Group 144A. The inner surface is moderately densely covered with silvery-white lanate hairs giving an effective color of near White Group 155C with a light greenish hue as the hairs overlay a green base of near Greyed-Green Group 191A shading to near Greyed-Green Group 191B.

*Peduncle.*—Length: commonly approximately 4.2 to 8.2 cm (approximately 5.7 cm on average). Diameter: commonly approximately 2.5 to 3.8 mm (approximately 3 mm) on average. Color: near Yellow-Green Group 144A.

*Buds.*—Shape: sub-globose to ovate to occasionally globose. Length: approximately 3 to 3.6 cm (approximately 3.4 cm on average) when the first sepal reflexes. Diameter: approximately 1.1 to 1.3 cm (approximately 1.3 cm on average) as the first sepal reflexes. Color: when first opening near and through Red Group 36A and 36B, and Orange Group 29C and 29D with some Red Group 40A at the petal edges.

*Flower.*—Shape: flat cup-shaped. Diameter: approximately 6 to 9 cm with an average of approximately 7.5 cm. Depth: approximately 2.6 cm for a fully open flower measured vertically from tip of the petals to the beginning of the receptacle. Texture: glabrous, opacus, and slightly unctuous, and physically slightly coriaceus to papyraceus. Arrangement: corollais polypetalous and rosulate. Color (when blooming): upper surface: a random mixture of small spots, larger blotches and streaks of near Red Group 40A, near Red Group 41D, near Red Group 43C, near Red Group 50B, near Orange-Red Group 32B, and near Orange-Red Group 33A, with Yellow Group 8A, and with increasing near Yellow Group 9A towards the petal base. Under surface: near Yellow Group 4D with shading near Yellow Group 4A and approaching Yellow Group 6A at the petal base. Small flecks of Red Group 39A and 39C commonly also are present. Fragrance: slight to moderately sweet. Petal number: approximately 24 to 41 on average under normal growing conditions. Petal size: commonly approximately 3.6 to 4.2 cm in length and approximately 2.1 to 3.9 cm in width. Petaloid number: commonly approximately 5 to 18 per flower. Petaloid size: commonly approximately 1.1 to 2.3 cm in length and approximately 0.4 to 0.9 cm in width. Petal shape: ovate to obovate. Stamen number: approximately 84 to 92 on average. Pistil number: approximately 55 to 59 on average. Lastingness: approximately 7 to 10 days on average on the plant, and approximately 5 to 7 days on average when cut and placed in a vase.

Development:

*Vegetation.*—The plant is a moderate grower. At West Grove, Pa. from Mid-May to Mid-September (a four-month growth period) the variety commonly forms shoots of approximately 65 to 75 cm in length.

*Blooming.*—Moderately abundant. A two year-old budded plant growing in the ground at West Grove, Pa. during June can be expected to produce approximately 20 to 35 open blossoms at one time.

*Resistance to diseases.*—Good with respect to common rose diseases.

*Aptitude to bear fruit.*—No fruit has been observed to date.

I claim:

1. A new and distinct variety of Floribunda rose plant characterized by the following combination of characteristics:

(a) an upright bushy growth habit, (b) abundantly forms attractive double flat cup-shaped bright multi-colored blossoms that are a distinctive random mixture in streaks and spots of red, orange, and yellow on the upper petal surfaces, (c) forms medium to dark green semi-glossy foliage, and (d) is particularly well suited for growing in an informal garden setting;

substantially as herein shown and described.

* * * * *

'Chrisgood'